United States Patent [19]

Bartholomew et al.

[11] Patent Number: 4,650,473
[45] Date of Patent: Mar. 17, 1987

[54] SUTURING SADDLE

[75] Inventors: Victor L. Bartholomew, Sandy; David J. Lentz, Salt Lake City, both of Utah

[73] Assignee: Warner-Lambert Company, Morris Plains, N.J.

[21] Appl. No.: 723,248

[22] Filed: Apr. 15, 1985

[51] Int. Cl.⁴ .......................... A61M 5/14; A61M 5/32
[52] U.S. Cl. ..................................... 604/174; 604/177; 604/93; 128/DIG. 26
[58] Field of Search ................. 604/174, 177, 179, 93, 604/175; 128/DIG. 26

[56] References Cited

U.S. PATENT DOCUMENTS

| 3,176,690 | 4/1965 | H'Doubler | 128/DIG. 26 |
| 3,777,761 | 12/1973 | Sheridan | 128/DIG. 26 |
| 3,903,895 | 9/1975 | Alley et al. | 128/DIG. 26 |
| 4,230,110 | 10/1980 | Beroff | 604/174 |
| 4,366,817 | 1/1983 | Thomas | 604/174 |
| 4,445,893 | 5/1984 | Bodicky | 604/177 |
| 4,479,796 | 10/1984 | Kallok | 604/175 |
| 4,563,177 | 1/1986 | Kamen | 604/177 |

Primary Examiner—Stephen C. Pellegrino
Assistant Examiner—John D. Ferros
Attorney, Agent, or Firm—Aaron Passman

[57] ABSTRACT

An adapter body for a catheter is described wherein the body is shaped to angle the catheter toward the blood vessel and maintain suturing about the body for holding same to the patient. In particular, a saddle is positioned across the top of the adapter body to locate a suture when same is used to tie down the adapter.

6 Claims, 6 Drawing Figures

SUTURING SADDLE

BACKGROUND OF THE DISCLOSURE

This disclosure relates to the hollow molded plastic adapter body which fits between a flexible plastic catheter and the out flow connection of the tube from an administration set. The adapter body is tapered and hollow having a diametrically larger inlet opening at the proximal end than the outlet opening at the distal end. Flexible wings extend from the adapter body for purposes of handling and then securing to the patient. At the distal end this adapter body is provided a fastener connection means such as luer lock threads about the proximal end inlet and a reduced tip for attachment to the end of a flexible catheter tube at the distal end outlet. In use, the adapter body is designed for an over-the-needle insertion procedure. That is to say that, the adapter and its catheter are coaxially carried by a hollow needle during insertion into a human blood vessel. The needle coaxially carries the catheter tightly thereabout and the two are inserted together as a unit with the needle tip penetrating and making an opening followed by the leading (distal) end of the catheter.

In order to facilitate this procedure, the tip of the catheter is chamfered or beveled so that as the needle is placed into the vein; it will easily carry with it the catheter. Similarly, the needle is beveled to facilitate penetration into the blood vessel and the orientation of the bevel relative to the adapter body is important due to the relationship between the wings and the needle. The needle bevel relative to the blood vessel lumen is such that the tip or point of the needle is furtherest from the skin surface during placement, for example, bevel upwardly. Once the catheter is placed within the vessel the needle can be axially extracted and this is done by holding the adapter body by, for example, placing the wings to which the catheter adapter is attached against the patient's flesh and withdrawing the needle by means of the flash back chamber attached at the end of the needle opposite the beveled point or tip.

Adapter bodies have been made with a variety of shapes and configurations such as for example, those shown in U.S. Pat. Nos. 3,348,544, 3,352,306, 3,406,685, 3,515,137, 3,595,230, 3,895,632, and 4,292,970. These shapes and configurations serve to facilitate handling and a variety of other useful purposes. However, none of these or other adapters have been specifically designed to guarantee suture securement of the catheter to the patient and/or the holding of same within the blood vessel.

In particular, the problem of the catheter inadvertently retracting from the blood vessel with blood loss or the loss of the intravenous site is a serious one since it threatens infection and/or bleeding. The additional pain caused to the patient from another catheter placement is also of great concern. As mentioned, catheter adapters have carried means for securement of same to the patient such as for example, wings for adhesive taping to the patient's skin. For suturing such wings have holes at their extremities. While the suturing technique is more secure than taping, wing suturing has problems. The holes in the wings are located laterally spaced away from the adapter body and when the wings are flexible, the displaced location of the holes can allow axial displacement of the adapter body. That is to say that, when the wings are made fragile and flexible in order to adapt to the contour of the patient's body. Suturing tied through the tips of the wings in the premade holes tends to aggravate a stress condition and give a loose attachment. The suture thread is very thin as is the cross section of the flexible wing, thus resulting in a potential for tearing either of the skin of the patient or the cross section of the wing.

OBJECTS OF THE DISCLOSURE

Consequently, an arrangement whereby the entire rigid body of the adapter can be securely affixed to the patient by means of a suture is required. The means of fixation should be adapted to resist the pull out of the catheter from the blood vessel and should hold the catheter in position to minimize the effects of internal lumen injury, such as abrasion, mechanical phlebitis, etc., i.e. to the inside surface of the blood vessel as a consequence of any relative motion between the catheter and the lumen.

In order to resolve the problems of the prior approaches and meet the needs of the product, a specifically shaped adapter body has been constructed in accordance with the description of the preferred embodiment which follows herein; such an adapter body satisfies the safety and performance needs heretofore unfulfilled.

SUMMARY OF THE INVENTION

An adapter is shown for use in combination with a catheter in an over-the-needle insertion procedure. The adapter includes laterally wings extending from an elongated hollow tubular body having distal and proximal end openings aligned along a common axis of the hollow tapered tubular body. The catheter is in fluid communication with and extends from the distal end opening of the hollow adapter body. The other end of the hollow tubular adapter body forms a fastener such as a luer lock connection. This facilitates the attachment of the adapter to the tubing fitting from an administration set for the introduction of for example, blood or saline. Along the patient contacting surface of the adapter body is a flat, generally planar, support surface that extends outwardly in a lateral fashion to form thin flexible wings.

The planar surface is angled relative to the axis of the adapter body in order to tip the distal end of the body toward the patient, thus positioning the catheter for location in the blood vessel. As a result of this angularity, the catheter extends from the body without kinking between its connection to the adapter tip and the entrance to the skin. The catheter axis lies generally along a line which is nearly parallel to the central axis of the blood vessel once the catheter is placed within the lumen. This is a consequence of the position of the planar surface of the adapter against the flesh.

Transverse to the axis of the adapter body opposite the planar surface is a saddle formed from a pair of upstanding ribs, a suture drawn between these ribs may be extended across the proximal portion of the wings at their juncture with the sides of the adapter body. The suture can also be sewn through the wings and into the flesh or skin of the patient. Either approach will assure that the adapter body and supported catheter will not move axially relative to the insertion site in the blood vessel.

The angular placement of the winged/planar surface is such that the radial extent of the luer lock fitting at the proximal end of the tubular adapter body and the radial extent of the catheter connection at the other end of the tubular body are generally in the plane of the wings whereby any concern about rocking of the catheter support adapter body either longitudinally or laterally is overcome by this particular geometric construction.

DETAILED DESCRIPTION OF THE DRAWINGS

Figure 1:
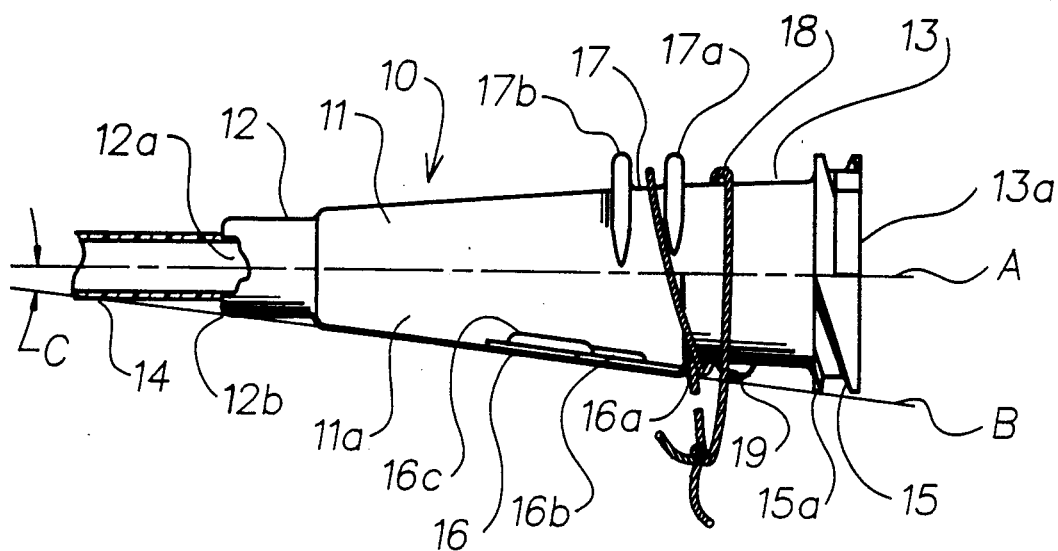
FIG. 1 is a side elevational view of the adapter of the preseut invention showing same sutured with a wrap and tie.
Figure 2:
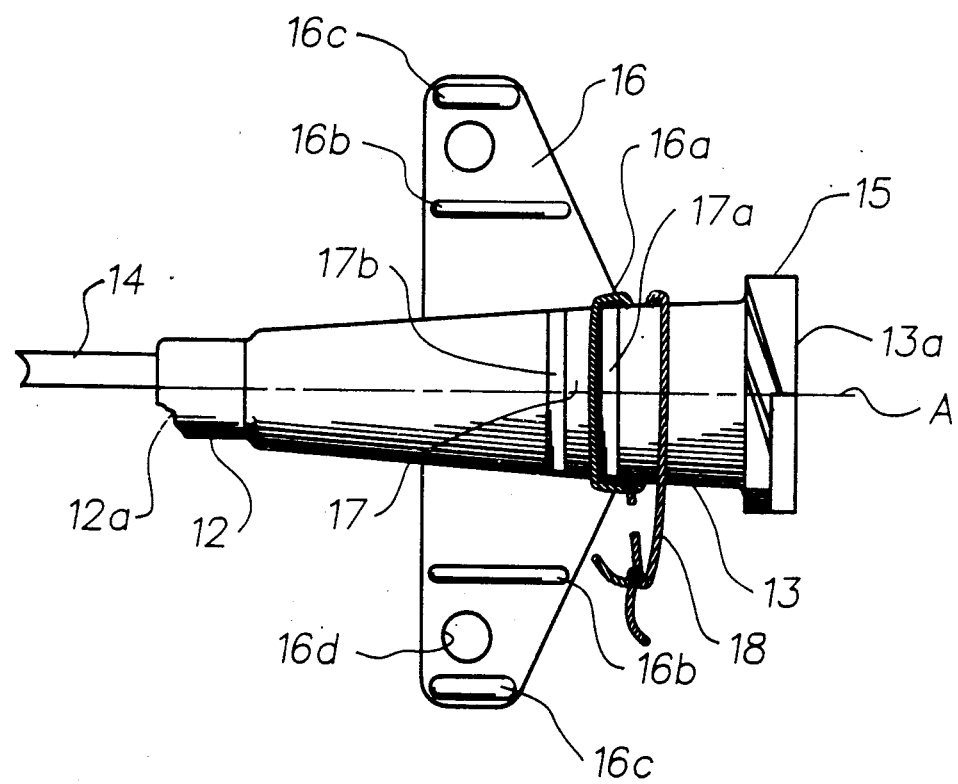
FIG. 2 is a top plan view of the adapter in FIG. 1.
Figure 3:
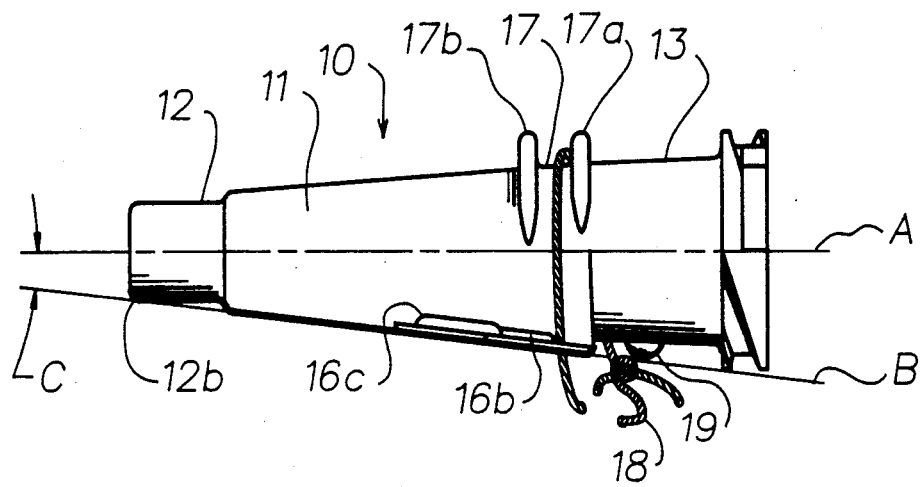
FIG. 3 is a side elevational view of the adapter of the present invention showing same with a suture passing through the wings close to the body.
Figure 4:
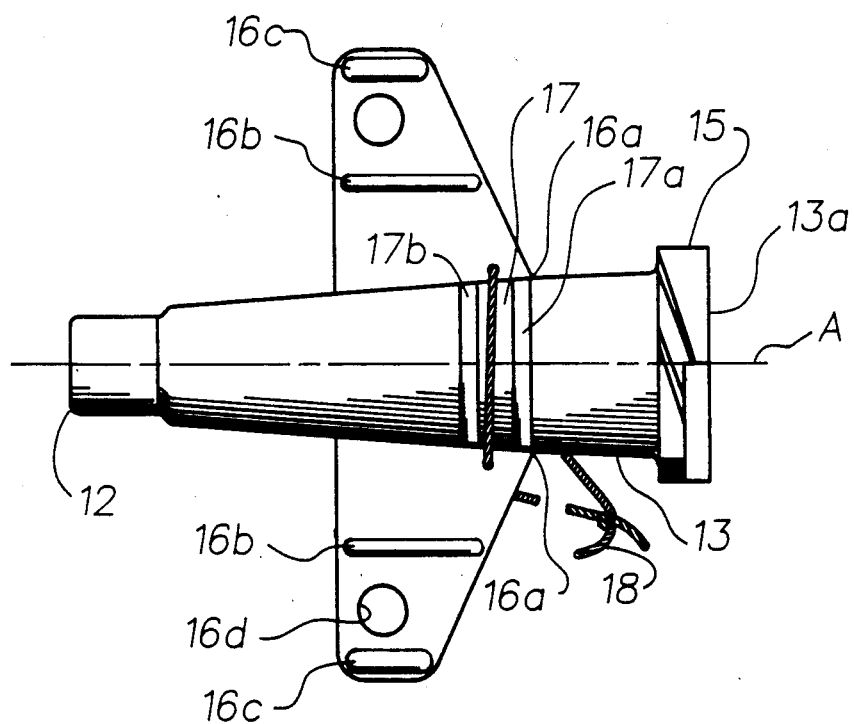
FIG. 4 is a top plan view of the sutured adapter in FIG. 3.
Figure 5:
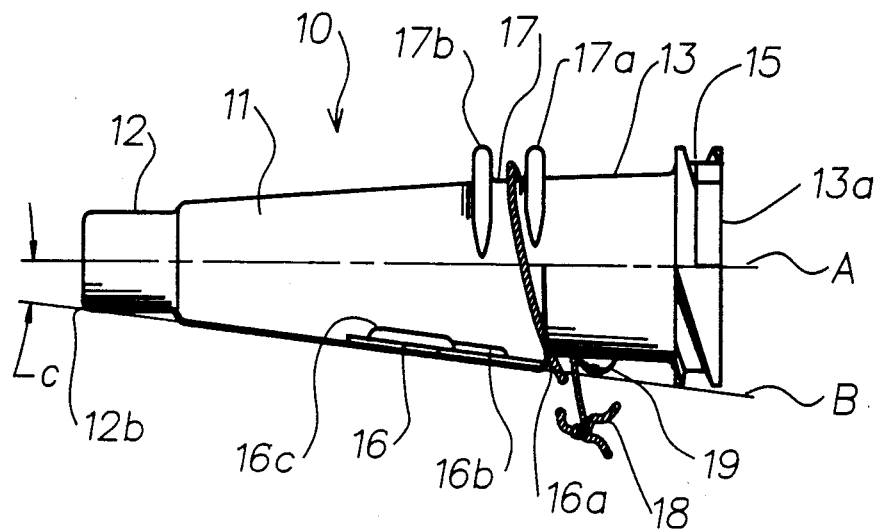
FIG. 5 is a side elevational view of the adapter of the present invention showing same with a suture once across the saddle and adjacent the body extending to the back of the wings.

FIGS. 1, 3, and 5 are similar side elevational views of the adapter 10, the only difference being the way in which the adapter is sutured, suture knots are not specifically shown. The main reference numbering for the parts in FIGS. 1 through 6 is identical.

Adapter 10 constructs of an elongated hollow tubular body 11 which is tapered about an axis A. The distal end 12 is small end and the proximal end 13 is the large end of body 11. The opening for the small or distal end 12 is designated 12a and shown best in FIG. 1 and the opening for the large end or proximal end 13 is designated 13a. Specifically, a portion of the catheter 14 is shown in section where it attaches to the distal end opening 12a also in section. The catheter 14 extends axially from opening 12a along axis "A" and has a bevelled or tapered tip to ease insertion in an over-the-needle technique during placement into a blood vessel.

At the proximal end 13 of the adapter body 11 there is provided a set of male luer lock threads 15 designed to receive the standard luer lock female nut. These threads are molded as part of the adapter body 11 and circumscribe the opening 13a at the proximal end 13 of the adapter 11. In FIGS. 1, 3, and 5, the radially extending portion 15a at the bottom of the threads 15 defines one point of a plane B (also shown in these figures). Another point in plane B is located at the distal end 12 and more specifically the radially extended portion of the bottom of the distal end opening designated 12b. While plane B is shown as merely a line in FIGS. 1, 3, and 5, and because more than two points are needed to describe a plane, it is clear from the top plan views in FIGS. 2, 4 and 6; that the wings 16 are in plane B and described at least a third point which is not on the line extending between portion 15a and 12b on the threads 15 and tip 12. The wings 16 are positioned to extend laterally from the base or patient contacting portion of the body 11. The wings are symmetric about the body having one wing on each side of the body opposite one another being the mirror image of one another. The angle C at which plane B intersects axis A as shown in FIGS. 1, 3, and 5 is approximately 6.75 degrees or about 7.0 degrees. The wings 16 are molded as part of the body and are thin. Flexibility of the wing results from the thin cross-section and the material selected. Longitudinal reinforcement ribs extend parallel to the axis of the axis A of the body 11 and inner rib is designated 16b and the outer rib near the tip of each wing is designated 16c. These ribs help constrain flexure of the wings. Disposed between the two ribs through the wing is a suturing hole 16d. The rear or proximal edge of the wing 16 where it joins the body 11 is called juncture 16a. This location is critical to the suturing function as will be explained in detail with respect to the suturing material. Wing 16 is positioned in plane B by the base or bottom of the body 11 immediately above the wing 16. Body 11 along its bottom is formed with an angled spacer 11a that extends radially from the axis to a greater extent at the proximal end than it does at the distal end where the body 11 meets the wing 16.

On the side of the body 11 opposite the wing 16 there is provided a saddle 17 formed by a pair of transversely extending upstanding ridges 17a and 17b. Ridges 17a and 17b define therebetween a saddle 17 and are positioned longitudinally relative to the body 11 such that ridge 17a is generally laterally in line with Juncture 16a. Ridge 17b is spaced forwardly therefrom at least two to three times the thickness of suturing material to permit same to be looped thereacross during securement of the adapter 10 to the patient. Suture material, fashioned of braided silk and having a diameter of 0.010 inches designated size 3-0 can be used for holding the adapter body 11. In FIGS. 1 through 6, the suturing material is generally designated 18 and may be any type of material generally used for surgical suturing whereby same can be wrapped, tied or sewn in any of the ways normally used by surgeons. The body 11 has one more feature to aid adapter 10 tie down and that is a hemispherically shaped downwardly depending nib 19 positioned between the radially extending portion 15a of the threads 15 and the area of juncture 16a i.e. between the rearwardly or proximal end of the wing 16 and the body 11. While only two ridges 17a and b are shown more could be provided.

As seen in FIGS. 1 and 2, the suture 18 is looped twice around the body 11; once through the saddle 17, and down through and between the nib 19 and the rearward juncture 16a before being secured by sewing through the flesh as indicated by a discontinuity in the suture material just beneath and aft of the wing 16 in FIGS. 1 or 2. This technique for suturing provides a fore and aft and a side to side securement of the adapter 10 to the patient. With regard to fore and aft or longitudinal movement, the point at which the suture 18 bears against the adapter 10 near juncture 16a, FIG. 1 prevents longitudinal movement which would pull the catheter 14 out of the patient's blood vessel. That is because the suture goes through the saddle 17 and bears against the rearward edge of the wings 16 at the juncture 16a with the body 11. Side to side or lateral movement is of course restrained by the way in which the suture 18 is tied to the patient. For purposes of clarity and illustration, this is shown merely by sewing the suture through the patient and out again. However, often times suturing material is tied to the patient through a small pinch of skin and then a leg or legs of suture are extended from the tie site to the adapter 10 and wrapped thereabout before being brought back to that tie site or to a different tie site. There are a multitude of possibilities of suturing techniques possible but to simplify illustration all are not shown.

FIGS. 3 and 4 show the same style adapter 10 with another suturing scheme in particular the suture 18 is here sewn directly through the wing 16 where same joins body 11 directly under the saddle 17, see FIG. 4. This is done by merely driving the suturing needle (not shown) through the adapter 10 at the wing 16. As the wing 16 is particularly flexible. Again the suture 18 holds the adapter body 11 from longitudinal movement by means of the securement due to the sewing through the wing 16 and subsequent connection to the patient by means of a site as shown by the discontinuity in the suture 18 illustrated essentially beneath or after the wing 16 in FIGS. 3 and 4.

Figure 6:
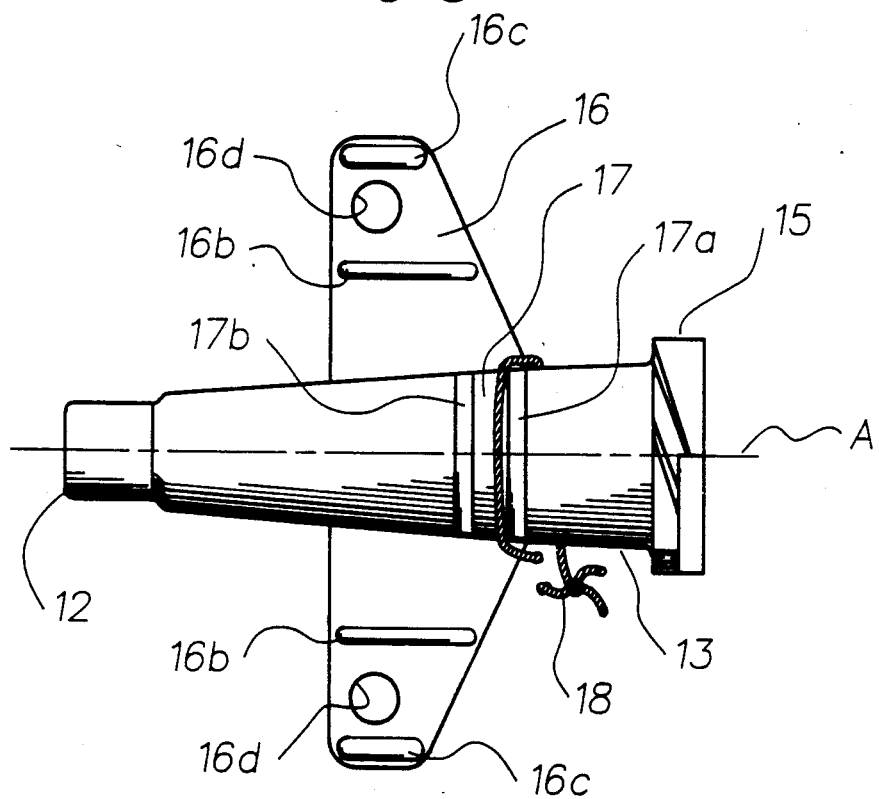
FIG. 6 is a top plan view of the adapter in FIG. 5.

Finally in FIGS. 5 and 6 a third possibility for securing the suture 18 relative to the patient is shown. In FIGS. 5 and 6 the suture 18 is again looped over the saddle 17 and across the Junctures 16a on both sides of the body 11 but the suture 18 is drawn across and under the body as shown in FIG. 5 to the tie site. This approach is similar to FIGS. 1 and 2 without the double wrap. The tie down to the patient in connection with FIGS. 5 and 6 is identical. Again the longitudinal movement is restrained by the positioning of the suture 18 relative to the juncture 16a near the body 11. The nib 19 once again acts to position the suture 18 where same drops beneath and across the bottom of the adapter 10.

While three specific methods of tying sutures relative to the adapter body 11 have been shown and described, the invention is the geometrical configuration of the adapter 10 which facilitates the use of suturing material to provide a securement of the adapter 10 to the patient thus preventing longitudinal withdrawal of the catheter from the blood vessel. Skilled artisans will no doubt conceive of a myriad of approaches useful to and which take advantage of the saddle 17 in cooperation with the angled wings 16 to provide a simple and secure attachment of the adapter 10 to the patient during catheterization. It is intended in the claim which follow that the structural and configurational features of the adapter 10 disclosed herein will be suitably protected for any and all purposes and functions to which the adapter 10 may be properly put in securing the catheter adapter.

What is claimed is:

1. A catheter support adapter in combination with a catheter for use in an over-the-needle insertion procedure comprising;

an elongated hollow tubular adapter body having distal end and proximal end openings aligned along the axis of said hollow tubular body,
a catheter connected to and extending from said distal end opening in fluid communication with said hollow body and being positioned along said axis for insertion into, for example, a human blood vessel via an over-the-needle technique,
fastening means positioned about said proximal end opening of said tubular body coaxially therewith and presenting a radially and outwardly extending portion established for conjugation with complimentary fastener means,
stabilizing means formed in a plane defined by the radial extent of said fastening means and said radially extended portion of said distal end and being positioned generally in a plane to form a surface apart from said axis and extending laterally away from said body but connected to said body at an angle relative to said axis,
saddle means located on said adapter body and positioned transverse to the axis of said body opposite said stabilizing means and across said body in a longitudinal position relative thereto and generally in-line with the longitudinally proximal portion of said stabilizing means for defining a lateral position to locate sutures relative to said stabilizing means so same may apply a holding force not only to pull the body axis toward the skin but to maintain said catheter in the vessel.

2. The body of claim 1 wherein said saddle means is defined by two or more upstanding ridges forming a saddle area therein directly opposite to said stabilizing means.

3. The body of claim 2 wherein the most proximal of said ridges is generally longitudinally aligned with the proximal portion of said stabilizing means.

4. The body of claim 1 wherein said stabilizing means have a thin cross section to permit the application of sutures transversely therethrough.

5. The body of claim 4 wherein said body is angled and carries said stabilizing means in said plane angled relative to said axis at about seven degrees.

6. The body of claim 1 wherein said body includes at least one nib extending radially from said body and positioned between said fastener means and said stabilizing means on the side of said body opposite said saddle means just aft of said stabilizing means so the outward extent of said nib is in said plane.

* * * * *